(12) United States Patent
Onoda (10) Patent No.: US 9,989,455 B2
(45) Date of Patent: Jun. 5, 2018

(54) METHOD OF TESTING ELECTRODE PASTE AND METHOD OF MANUFACTURING ELECTRODE

(71) Applicant: TOYOTA JIDOSHA KABUSHIKI KAISHA, Toyota-shi, Aichi-ken (JP)

(72) Inventor: Yusuke Onoda, Toyota (JP)

(73) Assignee: TOYOTA JIDOSHA KABUSHIKI KAISHA, Aichi-ken (JP)

( * ) Notice: Subject to any disclaimer, the term of this patent is extended or adjusted under 35 U.S.C. 154(b) by 214 days.

(21) Appl. No.: 14/853,403

(22) Filed: Sep. 14, 2015

(65) Prior Publication Data

US 2016/0084752 A1 Mar. 24, 2016

(30) Foreign Application Priority Data

Sep. 18, 2014 (JP) ................. 2014-190396

(51) Int. Cl.
*G01N 21/25* (2006.01)
*G01N 33/00* (2006.01)
*H01M 4/04* (2006.01)
*G01N 21/31* (2006.01)
(Continued)

(52) U.S. Cl.
CPC ............ *G01N 21/25* (2013.01); *G01N 15/06* (2013.01); *G01N 21/31* (2013.01); *G01N 33/00* (2013.01); *H01M 4/0404* (2013.01); *G01N 2015/0687* (2013.01); *G01N 2015/0693* (2013.01); *G01N 2033/0096* (2013.01); *H01M 10/052* (2013.01)

(58) Field of Classification Search
CPC ..................................... G01N 21/25

USPC ......................................... 356/402
See application file for complete search history.

(56) References Cited

U.S. PATENT DOCUMENTS

| 4,208,185 A * | 6/1980 | Sawai ................ G01N 33/48 356/246 |
| 2011/0017209 A1* | 1/2011 | Monzyk ............... A61M 16/10 128/202.26 |

(Continued)

FOREIGN PATENT DOCUMENTS

| JP | 2009252398 A | 10/2009 |
| JP | 2010-272287 A | 12/2010 |
| JP | 2011222299 A | 11/2011 |

*Primary Examiner* — Tarifur Chowdhury
*Assistant Examiner* — Omar Nixon
(74) *Attorney, Agent, or Firm* — Sughrue Mion, PLLC (57) ABSTRACT

A method of testing an electrode paste for producing an electrode for a secondary battery includes preparing an electrode paste obtained by kneading at least active material particles and water dispersible binder particles in an aqueous solvent; performing centrifugation on the electrode paste and collecting a supernatant containing the binder particles, and a free active material; and measuring an absorbance of the supernatant at an evaluation wavelength by using a spectrophotometer, wherein the evaluation wavelength is determined based on a relationship between an average particle size of the binder particles and the absorbance of the supernatant such that a proportion of an absorbance resulting from the binder particles in the absorbance of the supernatant becomes equal to or less than 30%, the relationship being determined in advance; and determining a quality of the electrode paste, based on the absorbance of the supernatant at the evaluation wavelength.

8 Claims, 7 Drawing Sheets

(51) Int. Cl.
*G01N 15/06* (2006.01)
*H01M 10/052* (2010.01)

(56) References Cited

U.S. PATENT DOCUMENTS

| 2013/0052530 | A1* | 2/2013 | Kitaguchi | H01M 4/13 |
| | | | | 429/211 |
| 2013/0266859 | A1* | 10/2013 | Todoriki | H01M 4/625 |
| | | | | 429/211 |
| 2013/0337320 | A1* | 12/2013 | Yukawa | H01M 4/0435 |
| | | | | 429/211 |
| 2014/0038041 | A1* | 2/2014 | Kajiwara | H01G 11/30 |
| | | | | 429/211 |

* cited by examiner

FIG. 6A SBR-A AVERAGE PARTICLE SIZE: 96nm

| | 400 | 500 | 600 | 700 | 800 | 900 |
|---|---|---|---|---|---|---|
| 400 | 29% | 23% | 20% | 17% | 15% | 14% |
| 500 | | 16% | 12% | 10% | 9% | 8% |
| 600 | | | 8% | 6% | 6% | 5% |
| 700 | | | | 4% | 4% | 4% |
| 800 | | | | | 4% | 4% |
| 900 | | | | | | 4% |

FIG. 6B SBR-A AVERAGE PARTICLE SIZE: 140nm

| | 400 | 500 | 600 | 700 | 800 | 900 |
|---|---|---|---|---|---|---|
| 400 | 52% | 46% | 40% | 36% | 32% | 29% |
| 500 | | 35% | 29% | 25% | 21% | 18% |
| 600 | | | 21% | 17% | 13% | 10% |
| 700 | | | | 11% | 7% | 5% |
| 800 | | | | | 3% | 1% |
| 900 | | | | | | -2% |

FIG. 6C SBR-A AVERAGE PARTICLE SIZE: 167nm

| | 400 | 500 | 600 | 700 | 800 | 900 |
|---|---|---|---|---|---|---|
| 400 | 51% | 46% | 43% | 39% | 36% | 34% |
| 500 | | 39% | 35% | 32% | 29% | 26% |
| 600 | | | 30% | 26% | 23% | 21% |
| 700 | | | | 22% | 18% | 16% |
| 800 | | | | | 15% | 13% |
| 900 | | | | | | 11% |

FIG. 6D SBR-A AVERAGE PARTICLE SIZE: 190nm

| | 400 | 500 | 600 | 700 | 800 | 900 |
|---|---|---|---|---|---|---|
| 400 | 60% | 55% | 51% | 47% | 44% | 41% |
| 500 | | 47% | 42% | 38% | 34% | 31% |
| 600 | | | 36% | 31% | 27% | 23% |
| 700 | | | | 25% | 21% | 17% |
| 800 | | | | | 16% | 13% |
| 900 | | | | | | 9% |

FIG. 6E SBR-A AVERAGE PARTICLE SIZE: 210nm

| | 400 | 500 | 600 | 700 | 800 | 900 |
|---|---|---|---|---|---|---|
| 400 | 70% | 66% | 62% | 58% | 55% | 52% |
| 500 | | 58% | 53% | 49% | 45% | 41% |
| 600 | | | 44% | 41% | 36% | 33% |
| 700 | | | | 36% | 29% | 26% |
| 800 | | | | | 22% | 20% |
| 900 | | | | | | 19% |

FIG. 6F SBR-A AVERAGE PARTICLE SIZE: 310nm

| | 400 | 500 | 600 | 700 | 800 | 900 |
|---|---|---|---|---|---|---|
| 400 | 86% | 84% | 82% | 81% | 79% | 78% |
| 500 | | 81% | 79% | 77% | 75% | 73% |
| 600 | | | 75% | 73% | 71% | 69% |
| 700 | | | | 69% | 67% | 65% |
| 800 | | | | | 64% | 61% |
| 900 | | | | | | 58% |

FIG.7

METHOD OF TESTING ELECTRODE PASTE AND METHOD OF MANUFACTURING ELECTRODE

INCORPORATION BY REFERENCE

The disclosure of Japanese Patent Application No. 2014-190396 filed on Sep. 18, 2014 including the specification, drawings and abstract is incorporated herein by reference in its entirety.

BACKGROUND OF THE INVENTION

1. Field of the Invention

The invention relates to a testing method for determining the quality of an electrode paste used for forming a secondary battery and to a method of manufacturing an electrode for the secondary battery, the method being related to the testing.

2. Description of Related Art

An electrode of a secondary battery includes a current collector which is composed of a metal material having good conductivity and an active material layer which is formed on the current collector. In a typical method for forming the active material layer, first, a primary kneaded material is prepared by kneading an active material and a thickener in an aqueous solvent. A binder is then added to the primary kneaded material, the resultant is further kneaded, and in this way, a composition in the form of a paste (an electrode paste) (the composition may also be a composition in the form of slurry or a composition in the form of ink; the same will be applied hereinafter) is prepared. A surface of a current collector is coated with the electrode paste obtained as described above, the electrode paste is then dried, and in this way, an active material layer is formed.

When the electrode paste is kneaded, the active material particles collide with each other in the solvent, and accordingly, the active material particles may undergo cracking, flaking, chipping, or the like. In such cases, the number of reactive sites on the surfaces of the active material particles is increased, and therefore thermal stability or durability is reduced in some cases. That is, the change in the properties of the electrode paste leads to a qualitative variation of the electrode and can consequently exert an influence on the battery performance. Accordingly, in order to stably manufacture a secondary battery that has good battery performance, a more homogenous electrode paste needs to be used. As a technique relating to this requirement, for example, Japanese Patent Application Publication No. 2010-272287 (JP 2010-272287 A) discloses a method of testing a negative electrode paste of a lithium secondary battery, in which the primary kneaded material as described above is subjected to centrifugation, the supernatant is collected, and from the results of spectral analysis of the supernatant, the quality of the primary kneaded material is evaluated (determined).

However, when a continuous kneading device such as an extrusion kneading device (extrusion kneader) is adopted, due to the constraints of facilities, it is difficult to collect the primary kneaded material, and the method in JP 2010-272287 A cannot be adopted. Furthermore, according to the examination conducted by the inventor, for example, in a case of using a water dispersible binder, when the electrode paste to which the binder has been added is tested, the quality of the electrode paste cannot be accurately determined with the method in JP 2010-272287 A.

SUMMARY OF THE INVENTION

The invention provides a testing method which makes it possible to evaluate a quality of an electrode paste prepared before a current collector is coated with the electrode paste so that a secondary battery having good battery performance is formed. The invention also provides a method of manufacturing an electrode for a secondary battery having good battery performance by screening out an electrode paste with a low quality through the aforementioned testing method and adopting an electrode paste having a high quality.

A first aspect of the invention relates to a method of testing an electrode paste for producing an electrode for a secondary battery. The method includes preparing an electrode paste obtained by kneading at least active material particles and water dispersible binder particles in an aqueous solvent; performing centrifugation on the electrode paste and collecting a supernatant containing the binder particles, and a free active material separated from the active material particles; and measuring an absorbance of the supernatant at an evaluation wavelength by using a spectrophotometer, wherein the evaluation wavelength is determined based on a relationship between an average particle size of the binder particles and the absorbance of the supernatant such that a proportion of an absorbance resulting from the binder particles in the absorbance of the supernatant becomes equal to or less than 30%, the relationship being determined in advance; and determining a quality of the electrode paste, based on the absorbance of the supernatant at the evaluation wavelength.

According to the method in the aforementioned aspect, it is possible to accurately evaluate the quality of the electrode paste prepared before a current collector is coated with the electrode paste (i.e., it is possible to accurately evaluate the quality of the electrode paste to which a binder has been added). That is, by measuring the absorbance of the supernatant at the evaluation wavelength determined based on the average particle size of the binder, the absorbance resulting from the binder can be reduced. As a result, the absorbance resulting from the free active material can be accurately measured, and it is possible to accurately determine the quality of the electrode paste. Furthermore, according to the method in the aforementioned aspect of the invention, it is possible to obtain an advantage in that the quality of the electrode paste can be evaluated even when there is difficulty in collecting the primary kneaded material.

The evaluation wavelength may be determined such that the evaluation wavelength satisfies an expression of W (nm)>Db (nm)×2.878+117.8, where W represents the evaluation wavelength, and Db represents the average particle size of the binder. When the evaluation wavelength is determined as described above, the absorbance resulting from the binder can be stably reduced, and the quality of the electrode paste can be more accurately determined. Considering the wavelength region measured by a general spectrophotometer, the evaluation wavelength W may be equal to or less than 900 nm.

The active material particles may be made of a graphite-based carbon material. The graphite-based carbon material has a highly oriented carbon hexagonal plane structure, and accordingly, unexpected cracking, chipping, or the like easily occurs at the time of kneading. Therefore, it is particularly useful to apply the technique disclosed herein to the material.

The electrode paste may contain a water-soluble thickener. When the electrode paste contains the thickener, an electrode with better durability can be manufactured. Furthermore, because the absorbance of the water-soluble thickener is extremely low (substantially zero), the accuracy of the quality determination can be maintained at a high level.

A plurality of the absorbances of the supernatant at a plurality of the evaluation wavelengths may be measured, and the quality of the electrode paste may be determined based on the plurality of the absorbances of the supernatant that are measured. When a plurality of measurement points are used, the evaluation can be performed with higher accuracy.

Determining the quality of the electrode paste may include calculating a difference between the measured absorbance of the supernatant and a reference value. In this case, when the difference is equal to or less than a predetermined threshold, the electrode paste is determined to have a high quality, and when the difference is greater than the predetermined threshold, the electrode paste is determined to have a low quality.

A second aspect of the invention relates to a method of manufacturing an electrode for a secondary battery, the electrode including a current collector and an active material layer on a surface of the current collector. The method includes forming an active material layer by coating the surface of the current collector with the electrode paste which has been determined to have a high quality by the testing method disclosed herein. As described above, according to the testing method disclosed herein, the quality of the electrode paste can be determined with high accuracy. Therefore, a secondary battery having good battery performance can be stably manufactured.

BRIEF DESCRIPTION OF THE DRAWINGS

Features, advantages, and technical and industrial significance of exemplary embodiments of the invention will be described below with reference to the accompanying drawings, in which like numerals denote like elements, and wherein.

DETAILED DESCRIPTION OF EMBODIMENTS

Hereinafter, embodiments of the invention will be described. Herein, matters (for example, general techniques relating to the preparation of a paste or an electrode), which are not included in the content specifically described in the present specification and are necessary for implementing the invention, can be regarded as matters of design determined by those skilled in the art based on the technique in related art in the pertinent technical field. The invention can be implemented based on both the disclosure of the present specification and the common technical knowledge in the related art.

In the present specification, a "secondary battery" collectively refers to batteries that can be repeatedly charged and discharged. Typical examples of the secondary battery mentioned herein include a so-called chemical battery such as a lithium ion secondary battery or a lithium ion capacitor and a so-called physical battery such as an electrical double layer capacitor.

In the present specification, the "average particle size" refers to a particle size corresponding to the particle size at a 50% cumulative value from a small particle size-side in a volume-based particle size distribution measured by a laser diffraction/light scattering method (that is, the average particle size is a 50% volume-average particle size which is also called a $D_{50}$ value or a median diameter).

(Electrode paste) First, the material constituting the electrode paste as a testing target will be described. Basically, the electrode paste contains an aqueous solvent, active material particles, and water dispersible binder particles.

Examples of the aqueous solvent include water and a mixed solvent containing water as a main component. As the solvent other than water that constitutes the mixed solvent, one kind or two or more kinds of organic solvents (for example, a lower alcohol and a lower ketone) that can be uniformly mixed with water can be appropriately selected and used. Among the solvents, an aqueous solvent is preferable in which water accounts for 80% by mass or more (preferably 90% by mass or more, and more preferably 95% by mass or more) of the total mass of the aqueous solvent.

As the active material particles, it is possible to use one kind or two or more kinds of materials among materials used as positive-electrode active materials or negative-electrode active materials of secondary batteries in related art.

For example, in a paste for forming a negative electrode (negative electrode paste) of a non-aqueous secondary battery or in an electrode paste of an electrical double layer capacitor, a granular carbon material (carbon particles) can be used. Specific examples of such a material include a graphitic material (graphite), a material based on hardly graphitizable carbon (hard carbon), a material based on easily graphitizable carbon (soft carbon), and a material having a structure of combination of the above materials. Among these, graphite-based carbon materials such as natural graphite, artificial graphite, mesocarbon microbeads (MCMB), and highly oriented graphite (HOPG) may be preferable. That is, because the graphite-based carbon materials have a highly oriented carbon hexagonal plane structure, unexpected cracking, chipping, or the like tends to easily occur particularly at the time of kneading. Therefore, it is particularly effective to apply the technique disclosed herein to such materials. Herein, in the present specification, the "graphite-based carbon material" is a generic term for a carbon material composed solely of graphite and a carbon material in which graphite accounts for 50% by mass or more (typically, 80% by mass or more, for example, 90% by mass or more) of the total mass of the carbon material.

Furthermore, for example, in a paste for forming a positive electrode (positive electrode paste) of a non-aqueous secondary battery, a granular lithium transition metal composite oxide material or a so-called olivine-based material can be used. Specific examples of such a material include $LiCoO_2$, $LiFeO_2$, $LiMn_2O_4$, $LiNi_{1/3}Co_{1/3}Mn_{1/3}O_2$, and $LiFePO_4$.

The average particle size of the active material particles is not particularly limited. However, typically, the average particle size of the active material particles can be approximately 1 μm to 20 μm (for example, 10 μm to 15 μm).

The binder particles are not particularly limited as long as they can be dispersed in water. As the binder particles, it is possible to use one kind or two or more kinds of materials among materials used for forming an electrode for a secondary battery in related art. Specific examples of such materials include rubber such as styrene butadiene rubber (SBR) and an acrylic acid-modified SBR resin (SBR-based latex); ethylene-based polymers such as polyethylene oxide (PEO) and polytetrafluoroethylene (PTFE); fluorine-based resins such as a tetrafluoroethylene-hexafluoropropylene copolymer (FEP) and a tetrafluoroethylene-perfluoroalkyl-vinylether copolymer (PFA); and a vinyl acetate copolymer. For example, in the negative electrode paste for a non-aqueous secondary battery, rubber such as SBR can be preferably used.

The average particle size Db of the binder particles is not particularly limited. However, typically, the average particle size Db of the binder particles can be equal to or greater than 50 nm (preferably equal to or greater than 80 nm and more preferably equal to or greater than 96 nm) and equal to or less than 300 nm (preferably equal to or less than 210 nm and more preferably equal to or less than 200 nm, for example, equal to or less than 190 nm). If the average particle size Db of the binder particles is within the above range, the testing method disclosed herein can be particularly preferably applied thereto. In other words, it is possible to determine the quality of the electrode paste (i.e., it is possible to determine whether the quality of the electrode paste is high or low), with higher accuracy. Furthermore, it is possible to obtain an advantage in that an electrode with higher durability (an electrode in which the active material layer has a high peel strength) can be manufactured.

The electrode paste can contain various additives (water-soluble additives) that are soluble in an aqueous solvent, in addition to the aforementioned materials. An example of such additives includes a thickener. Examples of the thickener include celluloses such as carboxymethyl cellulose (CMC), methyl cellulose (MC), cellulose acetate phthalate (CAP), hydroxypropyl methylcellulose (HPMC), and hydroxypropyl methylcellulose phthalate (HPMCP). If the electrode paste contains the thickener, it is possible to improve the workability at the time of kneading or to improve the stability of the electrode paste, and as a result, an electrode with better durability can be manufactured. Herein, the water-soluble additive can be regarded as having substantially no absorbance (the absorbance of the water-soluble additive can be regarded as being substantially zero).

(Method of testing electrode paste) Hereinafter, by using a negative electrode paste used for preparing a negative electrode for a non-aqueous secondary battery as an example, the testing method according to the embodiment disclosed herein will be specifically described with reference to drawings as appropriate. In the following drawings, the members or sites having the same effects are denoted by the same reference numerals so as not to repeat or to simplify the description thereof. Furthermore, the dimensional relationship (length, width, thickness, and the like) in each of the drawings does not reflect the actual dimensional relationship.

The method of testing the negative electrode paste disclosed herein roughly includes the following four steps consisting of 1. Preparation of negative electrode paste, 2. Collection and preparation of supernatant, 3. Measurement of absorbance, and 4. Determination of quality. The testing method can include other steps at any stage in addition to these steps.

(1. Preparation of negative electrode paste) In the testing method disclosed herein, first, a negative electrode paste is prepared. In an example, first, negative electrode active material particles and a thickener are kneaded in an aqueous solvent, thereby preparing a primary kneaded material. Second, water dispersible binder particles are added to the primary kneaded material to produce a mixture, and then the mixture is further kneaded, thereby preparing the negative electrode paste. Herein, because the materials (the negative electrode active material, the thickener, and the binder) constituting the negative electrode paste are the same as those described above, detailed description thereof will not be repeated.

The means for kneading is not particularly limited, and the general kneading methods that are used for preparing an electrode paste in related art can be used. For example, it is possible to use apparatuses called a kneading device, a stirrer, a grinder, a disperser, or a kneader. Particularly, in a case of employing continuous kneading means such as an extrusion kneading device (extrusion kneader), it is difficult to collect the primary kneaded material due to the constraints of facilities. Therefore, it is particularly effective to apply the technique disclosed herein in such a case.

Figure 1:
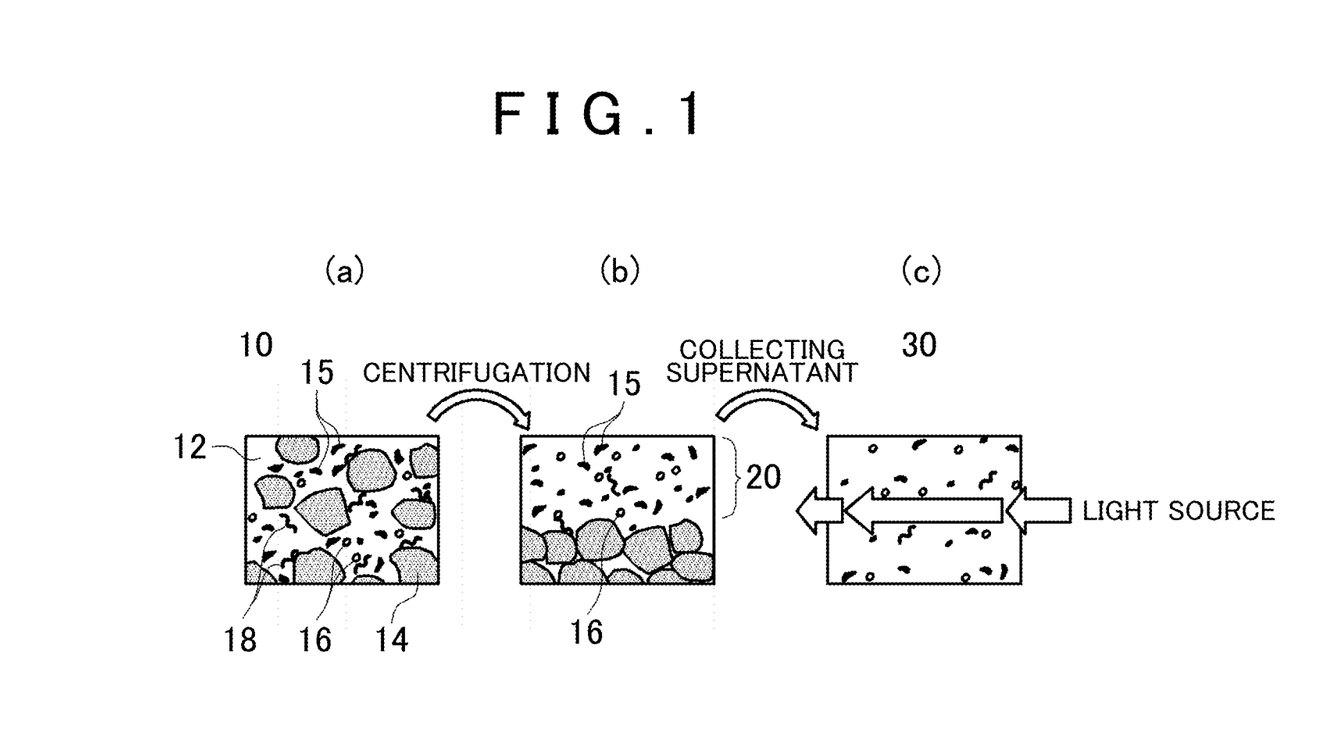
FIG. 1 schematically shows an electrode paste and a sample for measurement according to an embodiment.

A negative electrode paste 10 according to an example is shown in (a) in FIG. 1. The negative electrode paste 10 shown in (a) in FIG. 1 contains negative electrode active material particles 14, water dispersible binder particles 16, and a water-soluble thickener 18 in an aqueous solvent 12. The negative electrode paste 10 also contains a free active material 15. The free active material 15 is a material separated from the active material particles as a result of chipping or cracking of the active material particles 14 caused when the active material particles 14 strongly collide with each other at the time of kneading. In other words, the particle size of the free active material 15 can be much smaller than the average particle size of the active material particles 14 (typically, the particle size of the free active material 15 can be equal to or smaller than one fifth (⅕) of the average particle size of the active material particles 14, for example, equal to or smaller than one tenth (1/10) of the average particle size of the active material particles 14).

The solid content (the content of nonvolatile components, that is, a proportion of materials constituting the negative electrode active material layer) of the negative electrode paste is not particularly limited. However, considering the workability (coating properties) or productivity (drying time), the solid content can be adjusted to be approximately 40% by mass to 60% by mass (for example, approximately 50% by mass to 60% by mass).

According to the examination performed by the inventor, even if the negative electrode pastes 10 are constituted by the same materials, and a mixing ratio of the materials as well as the solid content are the same for the negative electrode pastes 10, the amounts of the free active material 15 contained in the negative electrode pastes 10 may be different from each other. Such variations in quality among the negative electrode pastes lead to variations in properties among the negative electrodes and thus exert an influence on the battery performance (for example, thermal stability or durability). In the testing method disclosed herein, by measuring the absorbance at an evaluation wavelength W, the amount of the free active material 15 is accurately determined. Consequently, the quality of the negative electrode paste can be accurately evaluated. Generally, as shear stress at the time of kneading is increased, a homogenous paste can be obtained within a shorter period of time, and this is advantageous from the viewpoint of productivity and cost. However, in a case in which high shear stress is applied at the time of kneading, adversely, a large amount of the free active material 15 tends to be generated. Therefore, it is particularly effective to apply the technique disclosed herein in such a case.

(2. Collection and preparation of supernatant) In the testing method disclosed herein, the negative electrode paste 10 is then subjected to centrifugation, and the supernatant is collected. The centrifugation conditions are not particularly limited. However, for example, the centrifugation may be performed for approximately 1 minute to 60 minutes (for example, 10 minutes to 30 minutes) with a centrifugal force of approximately 5000 G to 20000 G. The negative electrode paste 10 that has undergone centrifugation is shown in (b) in FIG. 1. As shown in (b) in FIG. 1, when centrifugation is performed, the active material particles 14 undergo sedimentation. At this time, a portion of the binder particles 16 can interact with the active material particles 14 and can undergo sedimentation together with the active material particles 14. In contrast, the upper portion of the negative electrode paste 10 is occupied by supernatant 20. Basically, the supernatant 20 contains the aqueous solvent 12, the free active material 15 which has been separated from the negative electrode active material particles, and the binder particles 16. In the example described herein, the supernatant 20 further contains the water-soluble thickener 18.

Herein, for example, when the concentration of the supernatant 20 is too high for measuring the absorbance as described later, the supernatant 20 may be appropriately diluted with the aqueous solvent 12. Generally, if the solid content of the negative electrode paste 10 is high, the absorbance tends to be high as well. For example, when the solid content of the negative electrode paste 10 is approximately 40% by mass to 60% by mass, the collected supernatant 20 may be diluted with the aqueous solvent 12 by approximately 1-fold to 50-fold (for example, 2-fold to 10-fold). In this way, the sample for measurement 30 shown in (c) in FIG. 1 can be prepared.

(3. Measurement of absorbance) In the testing method disclosed herein, the absorbance of the sample for measurement 30 (supernatant 20) at the evaluation wavelength W is then measured by using a spectrophotometer. Herein, the evaluation wavelength W is determined such that the proportion of the absorbance resulting from the binder particles 16 in the absorbance of the sample for measurement 30 becomes equal to or less than 30% (preferably equal to or less than 20%, more preferably equal to or less than 10%, and particularly preferably equal to or less than 5%). By reducing the absorbance resulting from the binder particles 16, the absorbance resulting from the free active material 15 can be accurately measured.

The evaluation wavelength W can be determined based on a relationship between the average particle size Db of the binder particles and the absorbance of the supernatant 20, the relationship being determined in advance. Specifically, for example, first, the aqueous solvent, the active material particles, the water dispersible binder particles, and the water-soluble thickener are prepared. The binder particles have a given average particle size Db. Then, the active material particles and the thickener are kneaded in the aqueous solvent, thereby preparing a blank solution. Furthermore, a portion of the blank solution is separated and mixed with the binder particles, and the mixture is further kneaded, thereby preparing a solution for measurement. At this time, the solid contents of the two kinds of solutions are made approximately equivalent to each other (within a margin of error of ±1%). Thereafter, by using a spectrophotometer, the absorbance of each of the two kinds of solutions at any evaluation wavelength is measured. The evaluation wavelength may include, for example, a wavelength in a range of approximately 400 nm to 900 nm (for example, in a region of visible light (380 nm to 780 nm)), although it also depends on the specifications of the spectrophotometer used. A single evaluation wavelength or a plurality of evaluation wavelengths may be used. Alternatively, continuous evaluation wavelengths (a region of evaluation wavelength) may be used. For example, in a region of evaluation wavelength from 400 nm to 900 nm, the evaluation wavelength may be set at intervals of 100 nm. Subsequently, at each evaluation wavelength, the absorbance of the blank solution is subtracted from the absorbance of each of the solutions for measurement, thereby calculating the absorbance resulting from the binder particles. Thereafter, from the following expression, (absorbance resulting from binder particles/absorbance of solution for measurement)×100, the proportion of the absorbance resulting from the binder particles in the absorbance of the solution for measurement can be obtained (see examples which will be described later). Then, the evaluation wavelength W is determined such that the absorbance resulting from the binder particles is reduced.

The inventor also examined a case of preparing the blank solution by kneading the thickener and the binder particles in the aqueous solvent. However, in this case, the measurement error was increased, and this led to a problem of not being able to accurately evaluate the free active material. That is, because the testing method disclosed herein makes it possible to accurately evaluate the quality of the electrode paste, it can be regarded as a better method.

The evaluation wavelength W is determined according to the average particle size Db of the binder particles. For example, the evaluation wavelength W may be determined such that it satisfies the following expression, W (nm)>Db (nm)×4.0−161.3 (Expression 0), where W>0 and Db>0. When the evaluation wavelength W is determined as above, the proportion of the absorbance resulting from the binder particles 16 in the absorbance of the solution for measurement can be reduced to a value which is approximately equal to or less than 40%. It is preferable that the evaluation wavelength W should be determined such that it satisfies the following expression, W (nm)>Db (nm)×2.878+117.8 (Expression 1). When the evaluation wavelength W is determined as above, the proportion of the absorbance resulting from the binder particles 16 in the absorbance of the sample for measurement can be reduced to a value which is approximately equal to or less than 30% in a stable manner. It is more preferable that the evaluation wavelength W should be determined such that it satisfies the following expression, W (nm)>Db (nm)×2.878+217.8 (Expression 2). When the evaluation wavelength W is determined as above, the proportion of the absorbance resulting from the binder particles 16 in the absorbance of the solution for measurement can be further reduced to a value which is, for example, approximately equal to or less than 20% in a stable manner.

In an example, the evaluation wavelength W is set to be equal to or less than 1000 nm (preferably equal to or less than 900 nm, for example, equal to or less than 800 nm) in consideration of the wavelength region measured by a general spectrophotometer. Furthermore, in another example, the evaluation wavelength W is set to be equal to or greater than 400 nm (for example, equal to or greater than 500 nm, preferably equal to or greater than 600 nm, and more preferably equal to or greater than 800 nm). When the evaluation wavelength W is set as described above, even if the average particle size Db of the binder particles 16 is relatively large, the measurement and evaluation can be appropriately performed.

A single evaluation wavelength W or two or more plural evaluation wavelengths W may be used. Alternatively, a region of continuous evaluation wavelengths can be set to be the evaluation wavelength W. From the viewpoint of improving the measurement accuracy, a plurality of evaluation wavelengths W or continuous evaluation wavelengths W may be set so as to take a plurality of absorbances into consideration. When two or more measurement points are used, the evaluation can be performed with higher accuracy.

(4. Determination of quality of negative electrode paste) In the testing method disclosed herein, the quality of the negative electrode paste 10 is determined (i.e., it is determined whether the quality of the negative electrode paste 10 is high or low), based on the aforementioned absorbance of the supernatant 20. Specifically, a reference value for determining a paste with a high quality is set. The method for setting the reference value is not particularly limited. However, for example, the reference value can be determined in consideration of the battery characteristics. Alternatively, the arithmetic mean, median, or the like of the absorbances of the supernatants of a plurality of negative electrode pastes can be employed as the reference value. Then, a difference between the reference value and the value of the absorbance measured is calculated. When the difference is equal to or less than a predetermined threshold, the negative electrode paste 10 is determined to have "a high quality", and when the difference is greater than the predetermined threshold, the negative electrode paste 10 is determined to have "a low quality". The threshold is not particularly limited because it also depends on the specifications of a battery as a target object. However, for example, the threshold can be set to be a value corresponding to approximately 2 σ to 4 σ (σ represents standard deviation). The negative electrode paste determined to have "a low quality" based on the determination results is removed (screened out), and as a result, it is possible to produce negative electrodes with a small qualitative variation. Consequently, secondary batteries having excellent battery performance can be stably provided.

(Method of manufacturing electrode) In other words, the invention provides a method of manufacturing an electrode for a secondary battery. In the manufacturing method, an active material layer is formed by using the electrode paste which has been determined to have a high quality by performing the testing method disclosed herein. Specifically, a surface of a current collector is coated with the electrode paste which has been determined to have a high quality, and the electrode paste is dried, thereby forming the active material layer on the current collector. In this way, an electrode can be manufactured.

As the current collector, conductive materials composed of a metal with excellent conductivity (for example, aluminum, copper, nickel, or stainless steel) can be preferably used. Furthermore, for the coating with the paste, for example, it is possible to use a coating apparatus known in related art such as a slit coater, a die coater, a comma coater, a gravure coater, or a dip coater. In addition, as a method for drying the paste, natural drying, drying with the use of hot air, air with low humidity, a vacuum, infrared rays, far infrared rays, or electron beams, and the like may be used alone or used in combination.

Due to the effect resulting from the use of the electrode paste which has been determined to have a high quality, the active material layer thus formed can be more homogenous than the active material layer in related art. Accordingly, in the secondary battery including the electrode disclosed herein, for example, the interface between the electrode and an electrolytic solution can be stably maintained, and excellent durability (for example, cycle characteristics) can be realized. Furthermore, in the secondary battery including the electrode disclosed herein, the problem such as deterioration of capacity or generation of gas does not easily occur even when the secondary battery is stored in, for example, a high-temperature environment for a long period of time, and the secondary battery can maintain and exhibit high battery performance over a long period of time. Therefore, a secondary battery that remains highly reliable over a long period of time can be efficiently provided.

Hereinafter, several test examples relating to the invention will be described, but the invention is not limited to the specific examples. Herein, as an example, a case of preparing and evaluating a negative electrode paste (a composition for forming a negative electrode active material layer) that can be used for preparing a negative electrode for a non-aqueous secondary battery was examined.

First, to a negative electrode active material (amorphous coated graphite powder) having an average particle size of 11.2 μm that contained natural graphite as a nucleus, carboxymethyl cellulose (CMC) as a thickener, and ion-exchanged water were added in this order, and the resultant was kneaded, thereby obtaining a primary kneaded material. Herein, a mass ratio between the active material and CMC (active material:CMC) was 100:1.0. For comparative examples, a portion of the primary kneaded material was collected in advance as a blank solution.

Thereafter, as binders, the following six kinds of styrene butadiene rubber (SBR-A to SBR-F) were prepared. The average particle size described below is a $D_{50}$ value based on a laser diffraction/light scattering method. SBR-A has an average particle size of 96 nm; SBR-B has an average particle size of 140 nm; SBR-C has an average particle size of 167 nm; SBR-D has an average particle size of 190 nm; SBR-E has an average particle size of 210 nm; and SBR-F has an average particle size of 310 nm Subsequently, the primary kneaded material obtained as above was separated, each of SBR-A to SBR-F was added thereto, and then ion-exchanged water was added thereto such that the final solid content thereof was adjusted to be 55%. Herein, the mass ratio among the active material, CMC, and SBR (the active material:CMC:SBR) was 100:1.0:1.0. Furthermore, the kneading conditions (shear strength, kneading time, and the like) were set to be the same for all of the negative electrode pastes. In this way, a total of six kinds of negative electrode pastes containing the negative electrode active material, CMC, SBR, and water were obtained.

Each of the negative electrode pastes was diluted with ion-exchanged water by 10-fold and then subjected to centrifugation for 20 minutes at 12000 G. Then, the supernatant was collected and further diluted with ion-exchanged water by 5-fold, thereby obtaining six kinds of solutions for measurement. Thereafter, by using a spectrophotometer (model: "V-650") manufactured by JASCO Corporation., the absorbance of each of the solutions for measurement was measured at evaluation wavelengths of 400 nm, 500 nm, 600 nm, 700 nm, 800 nm, and 900 nm.

Figure 2:
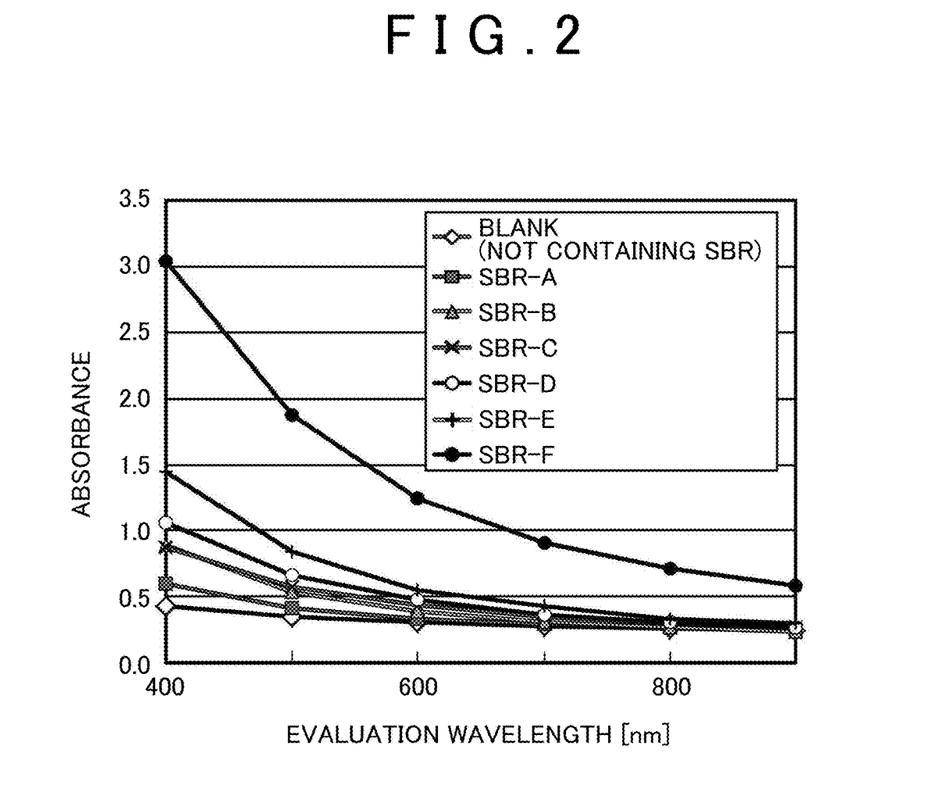
FIG. 2 is a graph showing a relationship between an evaluation wavelength and an absorbance.
Figure 3:
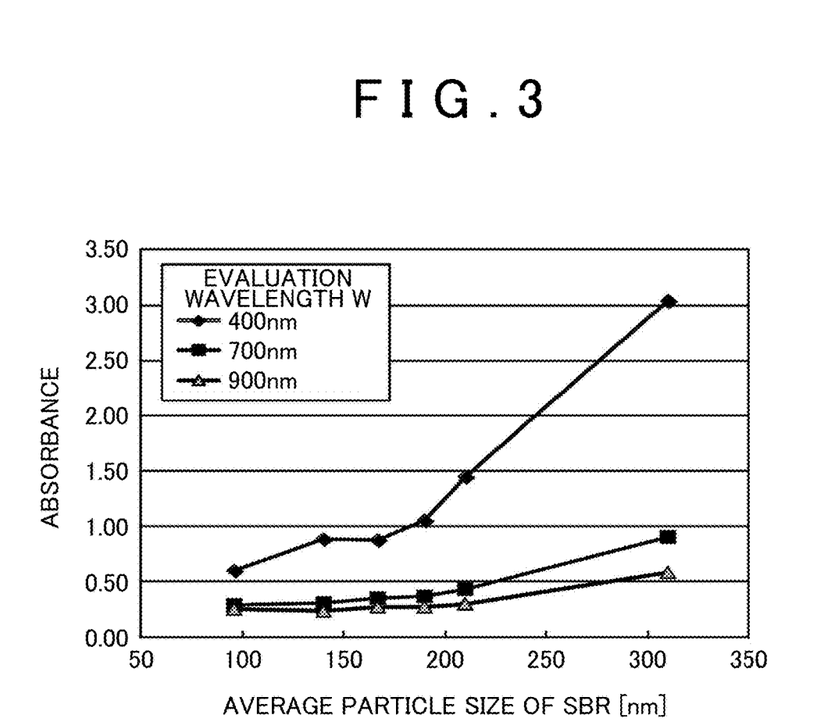
FIG. 3 is a graph showing a relationship between the average particle size of SBR and the absorbance.

FIG. 2 shows a relationship between the evaluation wavelength and the absorbance. FIG. 3 shows a relationship between the average particle size of SBR and the absorbance. As shown in FIGS. 2 and 3, the larger the average particle size of the SBR used, the greater the absorbance of the negative electrode paste. Particularly, when the average particle size of SBR exceeds 200 nm, the absorbance is greatly increased. Presumably, this is because in addition to the absorbance of the free active material that is originally focused on as a target of measurement, the absorbance resulting from SBR, for example, the absorbance of SBR or the absorbance of particles (aggregates), which are formed as a result of clustering of the free active material or CMC around SBR as a nucleus, makes a great contribution to the increase in the absorbance of the negative electrode paste.

Figure 4:
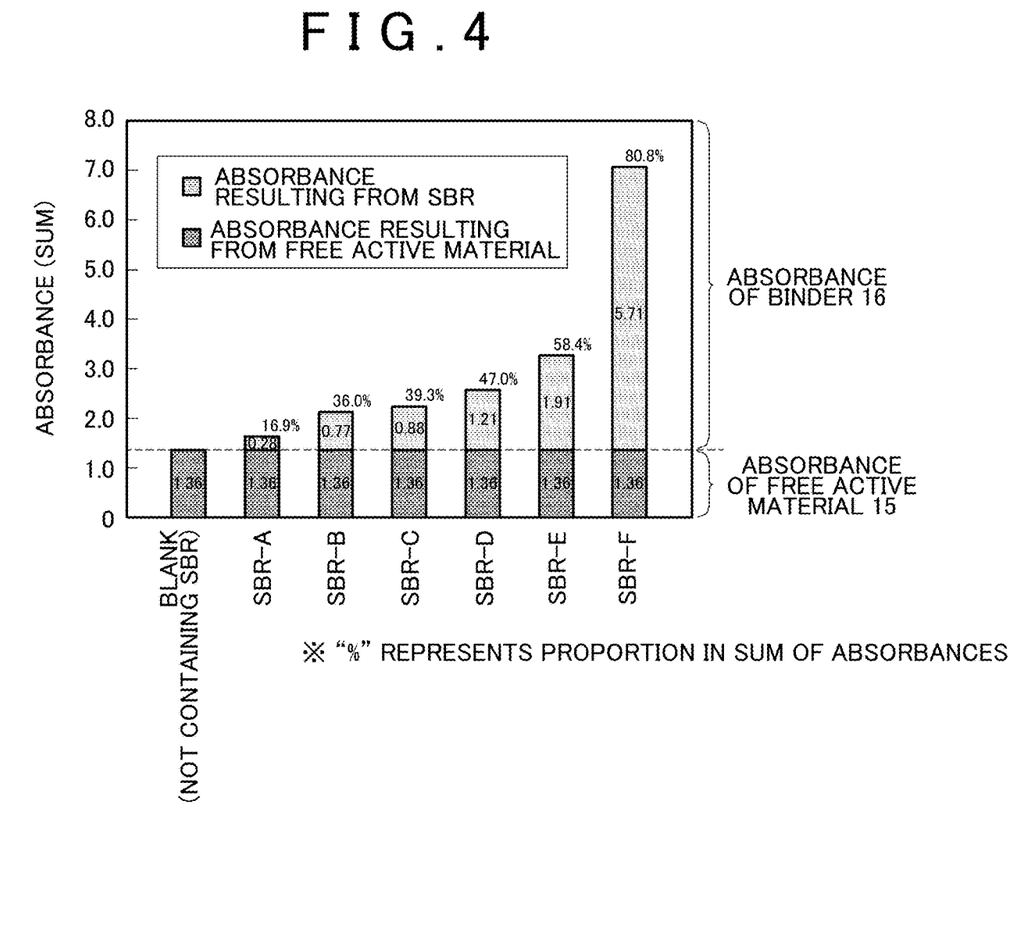
FIG. 4 is a graph showing the sum of absorbances obtained when four evaluation wavelengths, 400 nm, 500 nm, 600 nm, and 700 nm were used.

For example, FIG. 4 shows the sum of the absorbances obtained when four evaluation wavelengths, 400 nm, 500 nm, 600 nm, and 700 nm were used. That is, the negative electrode pastes are compared to each other based on the sum of the absorbance at an evaluation wavelength of 400 nm, the absorbance at an evaluation wavelength of 500 nm, the absorbance at an evaluation wavelength of 600 nm, and the absorbance at an evaluation wavelength of 700 nm. Herein, CMC is water-soluble, and the absorbance thereof is substantially zero. Therefore, the absorbance (1.36) of the blank solution can be roughly regarded as the absorbance resulting from the free active material. Accordingly, in FIG. 4, a value obtained by subtracting the absorbance (1.36) of the blank solution from the absorbance of each of the negative electrode pastes is described as the "absorbance resulting from SBR". Furthermore, FIG. 4 also shows the proportion (%) of the absorbance resulting from SBR in the absorbance of the negative electrode paste that is calculated from the following expression, (absorbance resulting from SBR/absorbance of negative electrode paste)×100.

As shown in FIG. 4, in the negative electrode paste containing SBR-A having an average particle size of 96 nm, the proportion of the absorbance resulting from SBR was low. In other words, it was understood that, in this negative electrode paste, when the evaluation wavelengths of 400 nm, 500 nm, 600 nm, and 700 nm were used, the absorbance resulting from the free active material could be accurately measured. In contrast, when SBR having a large average particle size was used, the proportion of the absorbance resulting from SBR was high, and thus the amount of the free active material could not be accurately detected.

Figure 5:
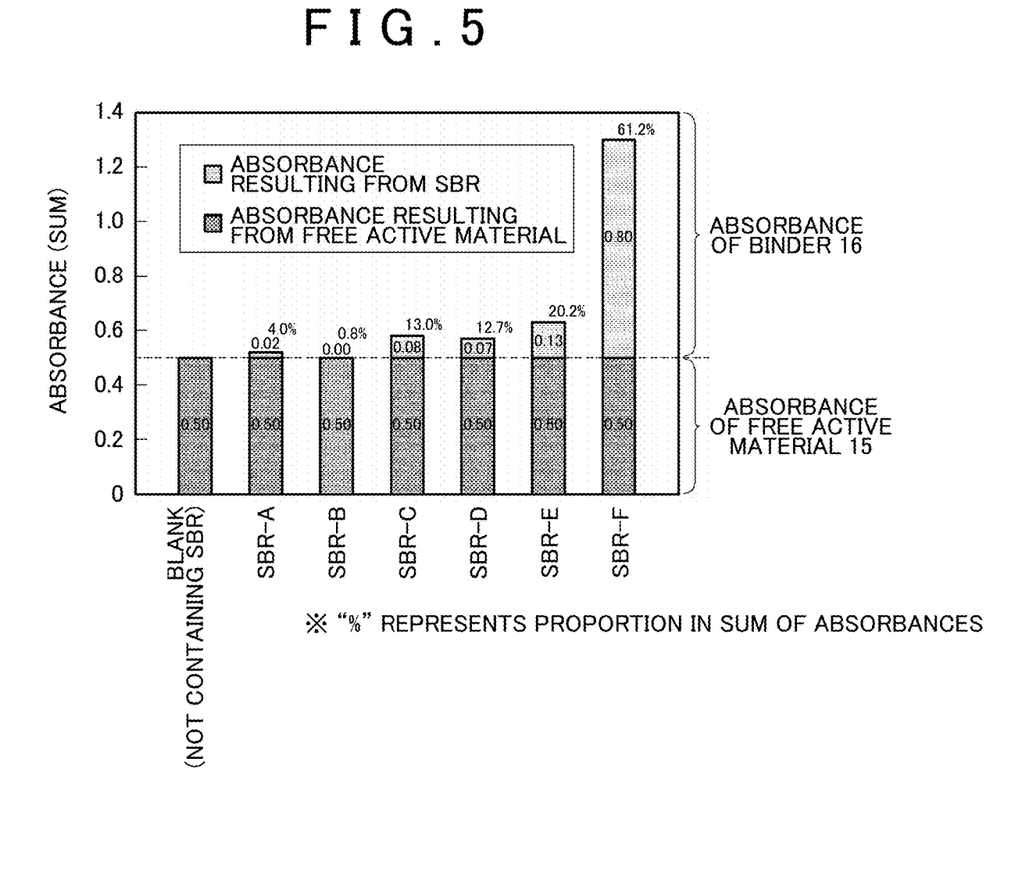
FIG. 5 is a graph showing the sum of absorbances obtained when two evaluation wavelengths, 800 nm and 900 nm were used.

As another example, FIG. 5 shows the sum of the absorbances obtained when two evaluation wavelengths, 800 nm and 900 nm were used. Herein, the method for calculating the absorbance resulting from SBR and the proportion thereof is similar to the calculation method used in the example shown in FIG. 4. As shown in FIG. 5, in the negative electrode pastes containing SBR having an average particle size of 96 nm to 210 nm, the proportion of the absorbance resulting from SBR was approximately 20% at most. In other words, it was understood that, in these negative electrode pastes, when the evaluation wavelengths of 800 nm and 900 nm were used, the absorbance resulting from the free active material could be accurately measured.

Figure 6A:
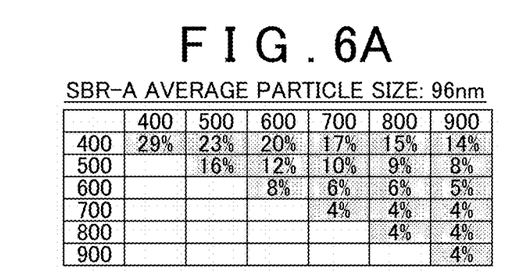
FIGS. 6A to 6F show a proportion of an absorbance resulting from SBR in the total absorbance, and show results obtained when SBR having different average particle sizes were used.
Figure 6B:
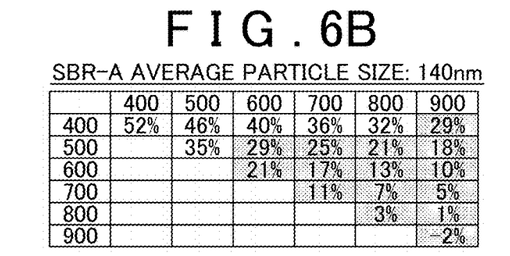
Figure 6C:
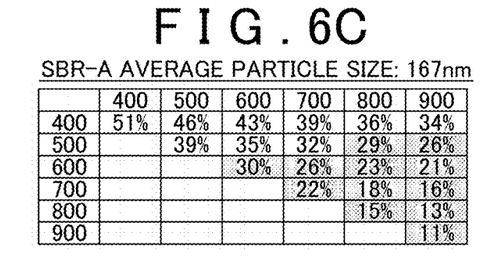
Figure 6D:
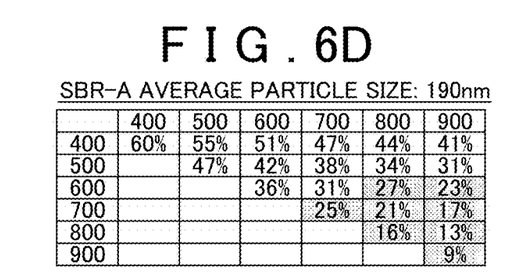
Figure 6E:
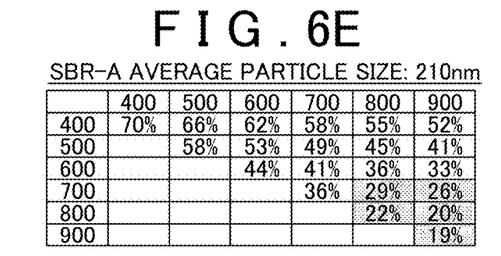
Figure 6F:
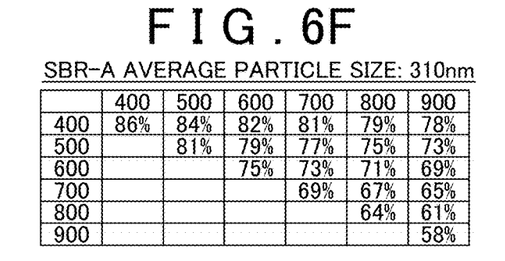

FIGS. 6A to 6F show the proportion (%) of the absorbance resulting from SBR calculated as described above, in the form of a chart. FIG. 6A shows the results obtained from the negative electrode paste containing SBR-A having an average particle size of 96 nm. FIG. 6B shows the results obtained from the negative electrode paste containing SBR-B having an average particle size of 140 nm. FIG. 6C shows the results obtained from the negative electrode paste containing SBR-C having an average particle size of 167 nm. FIG. 6D shows the results obtained from the negative electrode paste containing SBR-D having an average particle size of 190 nm. FIG. 6E shows the results obtained from the negative electrode paste containing SBR-E having an average particle size of 210 nm. FIG. 6F shows the results obtained from the negative electrode paste containing SBR-F having an average particle size of 310 nm. In each of the charts, the ordinate shows the initial point (nm) of the evaluation wavelength, and the abscissa shows the end point (nm) of the evaluation wavelength. For example, the proportion (%) of the absorbance shown in FIG. 4 corresponds to the cell where 400 nm on the ordinate and 700 nm on the abscissa cross each other. Moreover, for example, the proportion (%) of the absorbance shown in FIG. 5 corresponds to the cell where 800 nm on the ordinate and 900 nm on the abscissa cross each other. In addition, as an index, a case in which the proportion of the absorbance resulting from SBR is equal to or less than 30% is colored grey.

As shown in FIGS. 6A to 6F, as the average particle size of SBR increases, the evaluation wavelength, at which the proportion of the absorbance resulting from SBR is reduced to a value which is equal to or less than 30%, moves toward the lower right side in the chart. From this pattern, it was understood that when SBR having a large average particle size is used, the evaluation wavelength needs to be set to be a larger value.

Figure 7:
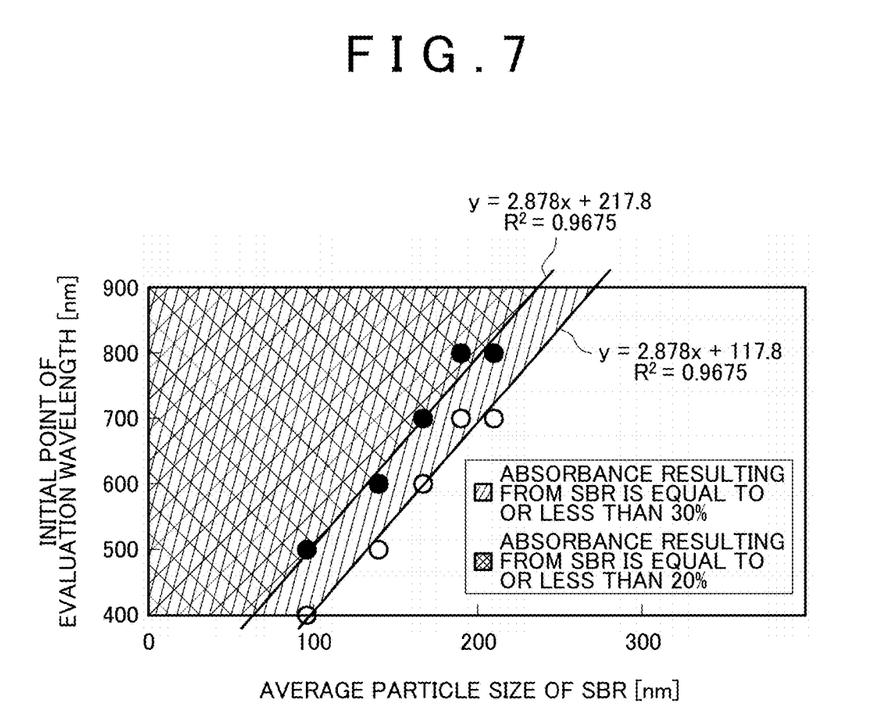
FIG. 7 is a graph showing a relationship between an initial point of an evaluation wavelength and the average particle size of SBR.

FIG. 7 shows a relationship between the initial point of the evaluation wavelength and the average particle size of SBR, based on the chart shown in FIGS. 6A to 6F. In FIG. 7, the ordinate shows the initial point (nm) of the evaluation wavelength, and the abscissa shows the average particle size (nm) of SBR. As is evident from FIG. 7, when the absorbance is measured at the evaluation wavelength that satisfies the following expression, W (nm)>Db (nm)×2.878+117.8 (Expression 1), the absorbance resulting from SBR can be reduced to a value which is approximately equal to or less than 30%. Preferably, by measuring the absorbance at the evaluation wavelength satisfying the following expression, W (nm)>Db (nm)×2.878+217.8 (Expression 2), the absorbance resulting from SBR can be reduced to a value which is approximately equal to or less than 20%. Consequently, it is possible to accurately detect the free active material and to accurately evaluate the quality of the negative electrode paste.

Hitherto, specific examples of the invention have been described in detail. However, they are merely examples and do not restrict the scopes of the claims of the invention. The techniques described in the claims include those obtained by modifying and changing the aforementioned specific examples in various ways.

What is claimed is:

1. A method of testing an electrode paste for producing an electrode for a secondary battery, comprising:
   preparing an electrode paste obtained by kneading at least active material particles and water dispersible binder particles in an aqueous solvent;
   performing centrifugation on the electrode paste and collecting a supernatant containing the binder particles, and a free active material separated from the active material particles; and
   measuring an absorbance of the supernatant at an evaluation wavelength by using a spectrophotometer, wherein the evaluation wavelength is determined based on a relationship between an average particle size of the binder particles and the absorbance of the supernatant such that a proportion of an absorbance resulting from the binder particles in the absorbance of the supernatant becomes equal to or less than 30%, the relationship being determined in advance; and determining a quality of the electrode paste, based on the absorbance of the supernatant at the evaluation wavelength.

2. The method according to claim 1, wherein the evaluation wavelength is determined such that the evaluation wavelength satisfies an expression of W (nm)>Db (nm)×2.878+117.8, where W represents the evaluation wavelength, and Db represents the average particle size of the binder particles.

3. The method according to claim 2, wherein the evaluation wavelength is equal to or less than 900 nm.

4. The method according to claim 1, wherein the active material particles are made of a graphite-based carbon material.

5. The method according to claim 1, wherein the electrode paste contains a water-soluble thickener.

6. The method according to claim 1, wherein a plurality of the absorbances of the supernatant at a plurality of the evaluation wavelengths are measured, and the quality of the electrode paste is determined based on the plurality of the absorbances of the supernatant that are measured.

7. The method according to claim 1, wherein determining the quality of the electrode paste includes calculating a difference between the measured absorbance of the supernatant and a reference value, wherein when the difference is equal to or less than a predetermined threshold, the electrode paste is determined to have a high quality, and when the difference is greater than the predetermined threshold, the electrode paste is determined to have a low quality.

8. A method of manufacturing an electrode for a secondary battery, the electrode including a current collector and an active material layer on a surface of the current collector, comprising forming the active material layer by coating the surface of the current collector with the electrode paste which has been determined to have a high quality by performing the method according to claim 1.

* * * * *